US009737446B2

(12) United States Patent
Hammons et al.

(10) Patent No.: US 9,737,446 B2
(45) Date of Patent: *Aug. 22, 2017

(54) ABSORBENT ARTICLE HAVING A LOTIONED TOPSHEET

(71) Applicant: The Procter & Gamble Company, Cincinnati, OH (US)

(72) Inventors: John Lee Hammons, Hamilton, OH (US); Raphael Warren, Amberley Village, OH (US); Ronald Bosman Visscher, Glendale, OH (US); Joseph Anthony Gatto, Loveland, OH (US); Brian Francis Gray, Wyoming, OH (US); Amy Marie Price, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 195 days.

This patent is subject to a terminal disclaimer.

(21) Appl. No.: 14/694,505

(22) Filed: Apr. 23, 2015

(65) Prior Publication Data

US 2015/0223998 A1 Aug. 13, 2015

Related U.S. Application Data

(63) Continuation of application No. 10/262,036, filed on Oct. 1, 2002, now Pat. No. 9,035,123.

(51) Int. Cl.
*A61F 13/84* (2006.01)
*A61F 13/511* (2006.01)
(Continued)

(52) U.S. Cl.
CPC ........ *A61F 13/51113* (2013.01); *A61L 15/225* (2013.01); *A61L 15/34* (2013.01);
(Continued)

(58) Field of Classification Search
CPC ............ A61F 13/2074; A61F 13/51113; A61F 13/8405; A61F 2013/15284;
(Continued)

(56) References Cited

U.S. PATENT DOCUMENTS 3,489,148 A 1/1970 Duncan et al.
3,896,807 A 7/1975 Buchalter
(Continued)

FOREIGN PATENT DOCUMENTS

DE 108036 9/1974
DE 3444464 1/1986
(Continued)

OTHER PUBLICATIONS

PCT International Search Report, mailed Feb. 20, 2004, 6 pages.

*Primary Examiner* — Lynne Anderson
(74) *Attorney, Agent, or Firm* — Andres E. Velarde (57) ABSTRACT

The absorbent article of the invention has a liquid impervious backsheet and a liquid pervious topsheet joined to the backsheet. The topsheet has an inner surface oriented toward the interior of the absorbent article and an outer surface oriented toward the skin and hair of the wearer when the absorbent article is being worn and an absorbent core positioned between the topsheet and the backsheet. At least a portion of the topsheet outer surface comprises an effective amount of a lotion coating which is semi-solid or solid at 20 degrees C., the lotion coating comprising:
(i) from about 10 to about 95% of a substantially water free emollient having a plastic or fluid consistency at 20 degrees C. wherein the emollient contains 5% or less water, the emollient comprising a member selected from the group consisting of petroleum-based emollients, fatty acid ester emollients, alkyl ethoxylate emollients, and mixtures thereof;
(ii) from about 5 to about 90% of an agent capable of immobilizing the emollient on the outer surface of the topsheet, the immobilizing agent being miscible with the emollient, the immobilizing agent having a melting point of at least about 35 degrees C. wherein the immobilizing agent is selected from the group consist-
(Continued)

ing of polyhydroxy fatty acid esters, polyhydroxy fatty acid amides, C14-C22 fatty alcohols, C14-C22 fatty acids, C14-C22 fatty alcohol ethoxylates with a degree of ethoxylation of 4 or less, and mixtures thereof.

29 Claims, 2 Drawing Sheets

(51) Int. Cl.
    *A61L 15/34*     (2006.01)
    *A61L 15/48*     (2006.01)
    *A61L 15/22*     (2006.01)
    *A61L 15/50*     (2006.01)

(52) U.S. Cl.
    CPC .............. *A61L 15/48* (2013.01); *A61L 15/50* (2013.01); *A61F 2013/8455* (2013.01); *A61F 2013/8458* (2013.01); *A61L 2400/10* (2013.01); *A61L 2420/00* (2013.01)

(58) Field of Classification Search
    CPC .... A61F 2013/51117; A61F 2013/8455; A61F 2013/8461; A61F 2013/8464; A61F 2013/8458
    See application file for complete search history.

(56) References Cited

U.S. PATENT DOCUMENTS

| | | | |
|---|---|---|---|
| 4,324,246 A | 4/1982 | Mullane et al. | |
| 4,609,518 A | 9/1986 | Curro et al. | |
| 4,626,254 A | 12/1986 | Widlund et al. | |
| 4,911,932 A | 3/1990 | Clum | |
| 5,445,823 A | 8/1995 | Hall | |
| 5,578,024 A | 11/1996 | Mizutani et al. | |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe | |
| 5,891,126 A | 4/1999 | Osborn et al. | |
| 5,932,212 A | 8/1999 | Khalaf | |
| 5,968,025 A | 10/1999 | Roe | |
| 5,998,032 A | 12/1999 | Hansen et al. | |
| 6,060,636 A | 5/2000 | Yahiaoui | |
| 6,107,537 A | 8/2000 | Elder et al. | |
| 6,118,041 A | 9/2000 | Roe et al. | |
| 6,120,783 A | 9/2000 | Roe | |
| 6,149,934 A | 11/2000 | Krzysik | |
| 6,153,209 A | 11/2000 | Vega | |
| 6,197,322 B1 | 3/2001 | Dutkiewicz | |
| 6,217,890 B1 | 4/2001 | Paul | |
| 6,238,682 B1 * | 5/2001 | Klofta ................... A01N 25/34 |
| | | | 424/401 |
| 6,340,411 B1 | 1/2002 | Hansen et al. | |
| 6,352,700 B1 | 3/2002 | Luu | |
| 6,426,444 B2 | 7/2002 | Roe et al. | |
| 6,436,418 B1 | 8/2002 | Sheldon | |
| 6,461,601 B1 | 10/2002 | Stoddart | |
| 6,475,197 B1 | 11/2002 | Krzysik | |
| 6,482,422 B1 | 11/2002 | Paul | |
| 6,485,733 B1 | 11/2002 | Huard | |
| 6,515,029 B1 | 2/2003 | Krzysik et al. | |
| 6,541,692 B2 | 4/2003 | Miller | |
| 6,586,652 B1 | 7/2003 | Roe et al. | |
| 6,706,946 B1 | 3/2004 | Lankhof | |
| 6,720,006 B2 | 4/2004 | Hanke et al. | |
| 6,756,520 B1 | 6/2004 | Krzysik et al. | |
| 6,825,393 B2 | 11/2004 | Roe et al. | |
| 6,861,571 B1 | 3/2005 | Roe et al. | |
| 6,888,044 B2 | 5/2005 | Fell et al. | |
| 7,166,292 B2 | 1/2007 | Isele et al. | |
| 9,035,123 B2 * | 5/2015 | Hammons ............... A61L 15/34 |
| | | | 604/359 |
| 2001/0009991 A1 | 7/2001 | Hisanaka | |
| 2002/0058917 A1 | 5/2002 | Hisanaka et al. | |
| 2002/0120241 A1 | 8/2002 | Tyrrell et al. | |
| 2002/0120242 A1 | 8/2002 | Tyrrell et al. | |
| 2003/0082219 A1 | 5/2003 | Warren et al. | |
| 2003/0206943 A1 | 11/2003 | Hammons et al. | |
| 2003/0206979 A1 | 11/2003 | Dvoracek et al. | |
| 2004/0167479 A1 | 8/2004 | Warren et al. | |
| 2004/0170589 A1 | 9/2004 | Gatto | |
| 2005/0010183 A1 | 1/2005 | Miller et al. | |
| 2005/0112078 A1 | 5/2005 | Boddupalli et al. | |
| 2005/0129651 A1 | 6/2005 | Gatto et al. | |
| 2005/0148962 A1 | 7/2005 | Warren et al. | |
| 2005/0154362 A1 | 7/2005 | Warren et al. | |
| 2006/0062816 A1 | 3/2006 | Gatto et al. | |
| 2006/0140899 A1 | 6/2006 | Koenig et al. | |
| 2006/0184150 A1 | 8/2006 | Noel | |
| 2007/0286876 A1 | 12/2007 | Warren et al. | |

FOREIGN PATENT DOCUMENTS

| | | |
|---|---|---|
| DE | 41 36 540 | 5/1992 |
| DE | 4401308 | 7/1995 |
| EP | 0 095 615 | 12/1983 |
| EP | 0 769 291 | 4/1997 |
| EP | 1 051 958 | 11/2000 |
| EP | 1120097 | 8/2001 |
| EP | 1 155 667 | 11/2001 |
| EP | 1 192 955 | 4/2002 |
| EP | 1 192 956 | 4/2002 |
| EP | 1 197 231 | 4/2002 |
| EP | 1 214 878 | 6/2002 |
| WO | WO 95/16824 | 6/1995 |
| WO | WO 95/35411 | 12/1995 |
| WO | WO 96/16681 | 6/1996 |
| WO | WO 96/16682 | 6/1996 |
| WO | WO 97/05908 | 2/1997 |
| WO | WO 97/05909 | 2/1997 |
| WO | WO 97/17060 | 5/1997 |
| WO | WO 98/24390 | 6/1998 |
| WO | WO 98/55158 | 12/1998 |
| WO | WO 98/55159 | 12/1998 |
| WO | WO 99/18919 | 4/1999 |
| WO | WO 99/32697 | 7/1999 |
| WO | WO 99/45973 | 9/1999 |
| WO | WO 99/45974 | 9/1999 |
| WO | WO 99/45976 | 9/1999 |
| WO | WO 99/53907 | 10/1999 |
| WO | WO 99/55303 | 11/1999 |
| WO | WO 00/01351 | 1/2000 |
| WO | WO 00/04870 | 2/2000 |
| WO | WO 00/10500 | 3/2000 |
| WO | WO 00/16733 | 3/2000 |
| WO | WO 00/27191 | 5/2000 |
| WO | WO 00/38626 | 7/2000 |
| WO | WO 00/38747 | 7/2000 |
| WO | WO 00/48544 | 8/2000 |
| WO | WO 00/64501 | 11/2000 |
| WO | WO 00/69485 | 11/2000 |
| WO | WO 01/00155 | 1/2001 |
| WO | WO 01/00156 | 1/2001 |
| WO | WO 01/00157 | 1/2001 |
| WO | WO 01/17564 | 3/2001 |
| WO | WO 01/17565 | 3/2001 |
| WO | WO 01/18181 | 3/2001 |
| WO | WO 01/43717 | 6/2001 |
| WO | WO 01/91684 | 12/2001 |
| WO | WO 02/22104 | 3/2002 |
| WO | WO 02/051456 | 7/2002 |
| WO | WO 02/076339 | 10/2002 |
| WO | WO 02/087517 | 11/2002 |
| WO | WO 03/028776 | 4/2003 |

* cited by examiner

ABSORBENT ARTICLE HAVING A LOTIONED TOPSHEET

FIELD OF THE INVENTION

This application relates to catamenial devices such as sanitary napkins for the absorption of menses. More particularly, the present invention relates to catamenial devices having a hydrophobic lotion coating on the outer surface of the topsheet that is transferable to the wearer's skin and hair by normal contact and wearer motion and/or body heat.

BACKGROUND OF THE INVENTION

Disposable absorbent articles, such as diapers, training pants, and catamenial devices having lotioned topsheets are known. Lotions of various types are known to provide various skin and hair benefits, such as prevention or treatment of diaper rash. These lotions can be applied to the topsheet of absorbent articles, for example, and can be transferred to the skin and hair of the wearer during use.

Unlike many types of disposable absorbent articles, catamenial devices, such as pads and pantyliners are specifically designed to acquire menstrual fluid. Menstrual fluid differs from other exudates, such as urine, in many important properties, such as viscosity. Therefore, catamenial devices should differ in their structural components from such devices as baby diapers to be optimized for the maximum absorption of menstrual fluid.

The addition of lotion to the topsheet of absorbent articles is known to provide benefits such as easier BM clean up on babies. Likewise, lotion on topsheets is known to provide for better skin and hair health of babies, such as the reduction of diaper rash. For example, U.S. Pat. No. 3,489,148 to Duncan et al. teaches a baby diaper comprising a hydrophobic and oleophobic topsheet wherein a portion of the topsheet is coated with a discontinuous film of oleaginous material. A major disadvantage of the diapers disclosed in the Duncan et al. reference is that the hydrophobic and oleophobic topsheets are slow in promoting transfer of urine to the underlying absorbent cores.

One successful attempt at overcoming the problems of Duncan is disclosed in Roe et al., U.S. Pat. No. 5,968,025. Roe et al. discloses an absorbent article in which a lotion is applied to a hydrophilic topsheet (or a topsheet rendered to be hydrophilic). The hydrophilic topsheet aids in ensuring urine gushes are adequately absorbed into the underlying core, rather than running off into the sides of a baby diaper, for example.

The known attempts at applying lotions to topsheets of absorbent products have been primarily directed to baby diapers, with the benefit provided being better skin health for the bottom of the baby. Little attention has been directed to the unique problems associated with the skin of an adult woman when wearing a catamenial pad. The skin of the vulvar area of an adult woman is very different than that of a baby's bottom (or buttock skin in general), and the lotion needs are very different. For example, rather than being concerned with diaper rash, a menstruating woman is more concerned about hygiene, that is, reducing the amount of menses remaining on the skin and hair after use of a sanitary pad.

The aforementioned attempts at providing a lotion on a topsheet of an absorbent article have focused on the lotion/topsheet characteristics necessary to handle a gush of urine in a relatively short amount of time. However, for catamenial devices, the fluid insult has very different characteristics, in the context of physio-chemical properties (e.g., viscosity, fluid dynamics, etc.) and in the volume and in the time to be absorbed. For example, menstrual flow typically consists of two patterns. One of these is "trickle" flow, which varies from 0.1 to 2 ml per hour. The second pattern is "gush" flow which varies from a few ml in volume delivered over a few seconds. Gush flow can result from an accumulation of menses pooling in the vagina which can then exit the body upon a change in position, such as a transition from sitting to standing. In any event, even with gush flow, the total amount of fluid required to be absorbed into the core in a given time is much less than that required by other absorbent products, such as baby diapers, for example. One practical result is that catamenial devices, rather than needing to be designed to handle gushing fluid, more typically handle fluid through a "blotting" effect.

Accordingly, there is a need for an improvement in catamenial devices to improve the skin and hair hygiene of menstruating women.

Additionally, there is a need for a catamenial device having improved fluid handling such that more menses enter into and remain in the device, and less on the skin and hair of the wearer.

Further, there is a need for a catamenial device that that can change the skin and hair/device interface properties when the device is worn.

SUMMARY OF THE INVENTION

The absorbent article of the invention has a liquid impervious backsheet and a liquid pervious topsheet joined to the backsheet. The topsheet has an inner surface oriented toward the interior of the absorbent article and an outer surface oriented toward the skin and hair of the wearer when the absorbent article is being worn and an absorbent core positioned between the topsheet and the backsheet. At least a portion of the topsheet outer surface comprises an effective amount of a lotion coating which is semi-solid or solid at 20 degrees C., the lotion coating comprising:

(i) from about 10 to about 95% of a substantially water free emollient having a plastic or fluid consistency at 20 degrees C. wherein the emollient contains 5% or less water, the emollient comprising a member selected from the group consisting of petroleum-based emollients, fatty acid ester emollients, alkyl ethoxylate emollients, and mixtures thereof;

(ii) from about 5 to about 90% of an agent capable of immobilizing the emollient on the outer surface of the topsheet, the immobilizing agent being miscible with the emollient, the immobilizing agent having a melting point of at least about 35 degrees C. wherein the immobilizing agent is selected from the group consisting of polyhydroxy fatty acid esters, polyhydroxy fatty acid amides, C14-C22 fatty alcohols, C14-C22 fatty acids, C14-C22 fatty alcohol ethoxylates with a degree of ethoxylation of 4 or less, and mixtures thereof.

BRIEF DESCRIPTION OF THE DRAWING

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, ratios and proportions used herein are by weight unless otherwise specified.

As used herein, the term "absorbent article" refers to catamenial devices that absorb and contain body exudates, primarily menses. The term "disposable" is used herein to describe absorbent articles which are not intended to be laundered or otherwise restored or reused as an absorbent article after a single use. Examples of catamenials include feminine hygiene garments such as sanitary napkins, pantiliners, interlabial devices and the like.

Disposable absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn toward or placed adjacent to the wearer's undergarments when the disposable absorbent article is worn.

Figure 1:
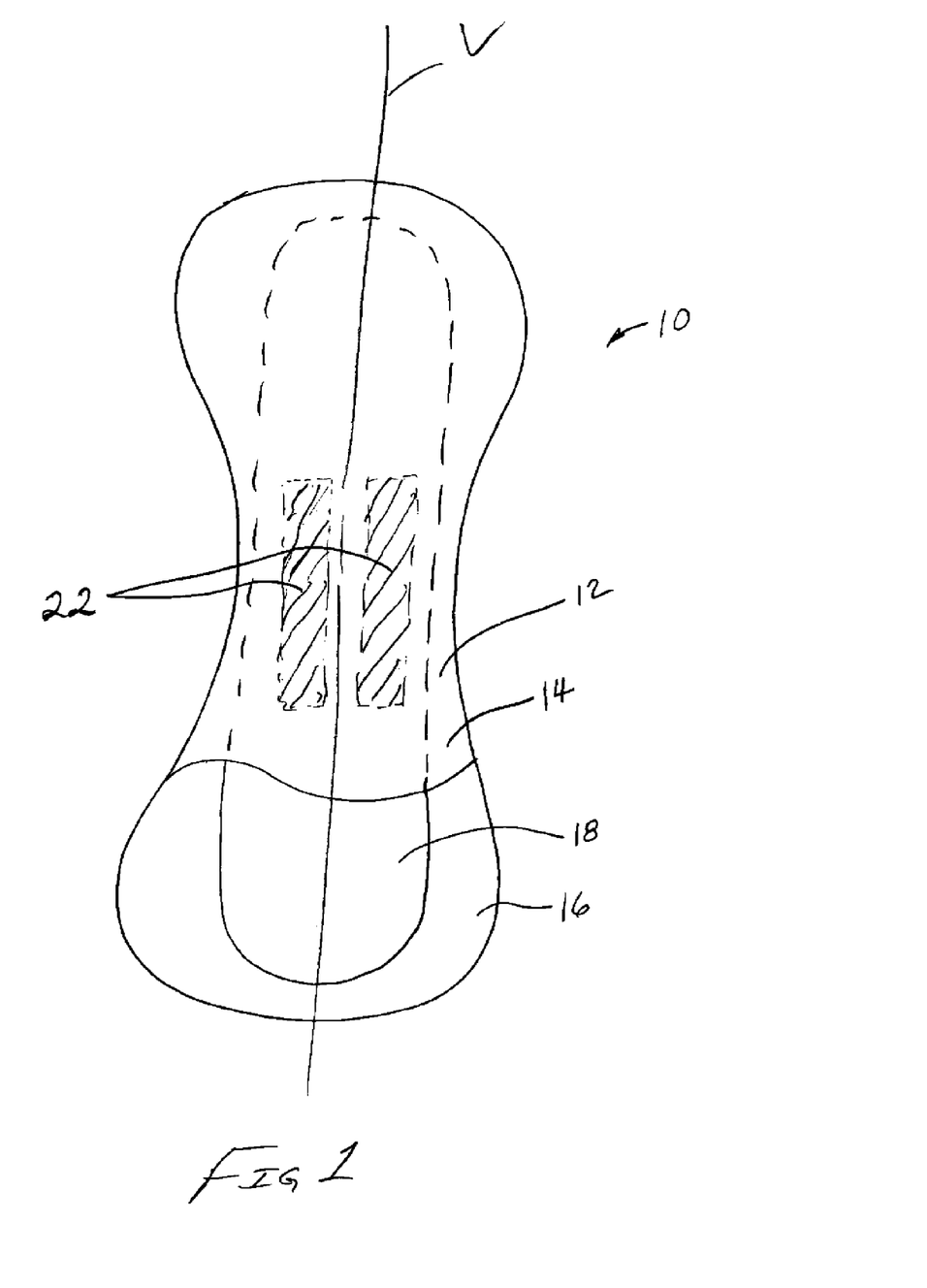
FIG. 1 is a perspective, partially cut-away view of a catamenial device having a topsheet and a lotion composition.

FIG. 1 shows a catamenial device 10, that can be a sanitary napkin or pantyliner, having a body-contacting surface 12 comprising a topsheet 14, a liquid impervious backsheet 16 joined to the topsheet 14, an absorbent core 18. The sanitary napkin 10 has a longitudinal axis L and may also be provided with additional features commonly found in napkins, including "wings" or "flaps" (not shown) as is known in the art, and, and/or a fluid acquisition layer to promote fluid transport to the absorbent core 18. Likewise, the topsheet of the sanitary napkin can have various optional characteristics, as is known in the art. For example, the topsheet 14 can have channels embossed therein to direct fluid flow, and can have apertures therethrough to aid in fluid acquisition. The topsheet 14 of the catamenial device 10 of the present invention has a lotion composition 22 disposed onto the topsheet.

The topsheet 14 and lotion composition 22 of the present invention offer significant advantages over known topsheets and lotions. In particular, in a preferred embodiment, the topsheet 14 is hydrophobic or rendered to be hydrophobic, and the lotion is also hydrophobic. The levels of hydrohobicity can be determined by standard techniques, such as measuring angles that a drop of water make on a surface of material. In general, for the purposes of this invention, a material is considered hydrophobic if a drop of water exhibits an angle of about 60 degrees or greater, as discussed more fully below. The levels of hydrophobicity of the topsheet and lotion, respectively, can be equal, or the hydrophobicity of the lotion can be greater than the hydrophobicity of the topsheet. In use, the lotion can transfer from the topsheet to the skin and hair of the wearer, which serves to make the skin and hair hydrophobic as well.

The advantage of the present invention can be appreciated with an understanding of the difference between menstrual fluid flow and urine flow in babies, for example. Topsheets of baby diapers are generally taught to be hydrophilic, with or without a lotion applied, such that sudden gushes of urine can be acquired through the topsheet and into the core with minimal runoff of fluid. However, it has been discovered that menstrual fluid, which has much lower fluid flow, both in quantity and time, can be very effectively handled with a hydrophobic topsheet. Whereas urine may simply run off of a hydrophobic topsheet, particularly one that is treated with a hydrophobic lotion, it has unexpectedly been found that such a structure provides for superior benefits in a catamenial pad for menstruating women. One superior benefit is cleaner skin and hair of the vulvar region after use of a catamenial device of the present invention. Another benefit is better fluid acquisition of the fluid due to transfer of the lotion to the skin and hair of the wearer that minimizes fluid transport on the skin and hair of the wearer away from the point of exit.

The topsheet is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material.

The backsheet and the topsheet are positioned adjacent the garment surface and the body surface, respectively, of the absorbent core. The absorbent core can be joined with the topsheet, the backsheet, or both in any manner as is known by attachment means (not shown in FIG. 1) such as those well known in the art. However, embodiments of the present invention are envisioned wherein portions of the entire absorbent core are unattached to either the topsheet, the backsheet, or both.

The topsheet of catamenial device 10 is preferably made of a hydrophobic material. Therefore, if the topsheet is a nonwoven, the constituent fibers are preferably hydrophobic. Fibers are considered to be hydrophobic if film sheets formed from the polymers of the fibers would exhibit contact angles with water greater than 60 degrees, more preferably 75 degrees, and even more preferably greater than about 90 degrees. Contact angles as a measure of hydrophobicity are well known in the art, and methods for measuring contact angles are equally well known. As is well known, contact angles greater than about 90 degrees are considered hydrophobic, and contact angles less than 90 degrees are often considered hydrophilic. As used herein, however, contact angles of 60 degrees or greater are considered hydrophobic.

The hydrophobic lotion compositions of the present invention are solid, or more often semisolid, at 20 degrees C., i.e. at ambient temperatures. By "semisolid" is meant that the lotion composition has a rheology typical of pseudoplastic or plastic fluids. When no shear is applied, the lotion compositions can have the appearance of a semi-solid but can be made to flow as the shear rate is increased. This is due to the fact that, while the lotion composition contains primarily solid components, it also includes some minor liquid components.

The lotion compositions of the present invention are at least semisolid solid at room temperature to minimize lotion migration. In addition, the compositions preferably have a final melting point (100% liquid) above potential "stressful" storage conditions that can be greater than 45 degrees C. (e.g., warehouse in Arizona, car trunk in Florida, etc.).

By being solid or semisolid at ambient temperatures, these lotion compositions do not have a tendency to flow and migrate into the interior of the sanitary napkin topsheet to which they are applied. This means less lotion composition is required for imparting desirable therapeutic or protective coating lotion benefits.

When applied to outer surface of sanitary napkin topsheets, the lotion compositions of the present invention can be transferable to the wearers skin and hair by normal contact, wearer motion, and/or body heat. Importantly, the lotions disclosed in the present invention reduce the adherence of menses to the skin and hair of the wearer, thereby reducing the amount of menses remaining on the body, that is, the skin and hair or hair of the wearer.

The sanitary napkin topsheets of the present invention contain an effective amount of the lotion composition. As used herein, the term "effective amount of a lotion coating" refers to an amount of a particular lotion composition which, when applied to a sanitary napkin topsheet, will be effective in reducing the adherence of menses to the skin and hair of the wearer. The effective amount of a lotion coating will depend, to a large extent, on the particular lotion composition used.

The lotion compositions of the present invention comprise: (1) an emollient(s); (2) an immobilizing agent(s) for the emollient; and (4) other optional components.

The viscosity of the formulated lotion compositions, including emollient, immobolizing agent, and optional components should be as high as possible to keep the lotion from flowing into the interior of the sanitary napkin. Unfortunately, high viscosities can also lead to lotion compositions that are difficult to apply without processing problems. Therefore, a balance must be achieved so the viscosities are high enough to keep the lotion compositions localized on the surface of the sanitary napkin topsheet, but not so high as to cause processing problems. Suitable viscosities for the lotion compositions will typically range from about 5 to about 200 centipoises, preferably from about 15 to about 100 centipoises, measured at 60 degrees C.

The key active ingredient in these lotion compositions is one or more emollients. As used herein, an emollient is a material that softens, soothes, supples, coats, lubricates, moisturizes, or cleanses the skin and hair. An emollient typically accomplishes several of these objectives such a soothing, moisturizing, and lubricating the skin and hair. For the purposes of the present invention, these emollients have either a plastic or fluid consistency at 20 degrees C., i.e., at ambient temperatures. This particular emollient consistency allows the lotion composition to impart a soft, lubricious, lotion-like feel.

The emollients useful in the present invention are also substantially free of water. By "substantially free of water" is meant that water is not intentionally added to the emollient. Addition of water to the emollient is not necessary in preparing or using the lotion compositions of the present invention and could require an additional drying step. However, minor or trace quantities of water in the emollient that are picked up as a result of, for example, ambient humidity can be tolerated without adverse effect. Typically, the emollients used in the present invention contain about 5% or less water, preferably about 1% or less water, most preferably about 0.5% or less water.

Emollients useful in the present invention can be petroleum-based, fatty acid ester type, alkyl ethoxylate type, fatty acid ester ethoxylates, fatty alcohol type, polysiloxane type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for lotion compositions of the present invention.

Suitable fatty acid ester type emollients include those derived from C14-C28 fatty acids, preferably C16-C22 saturated fatty acids, and short chain (C1-C8, preferably C1-C3) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols (C14-C28, preferably C14-C16) and shorter chain fatty acids e.g., lactic acid, such as lauryl lactate and cetyl lactate.

Suitable alkyl ethoxylate type emollients include C14-C22 fatty alcohol ethoxylates having an average degree of ethoxylation of 4 or less. Preferably, the fatty alcohol ethoxylate emollient is selected from the group consisting of lauryl, cetyl, and stearyl ethoxylates, and mixtures thereof, having an average degree of ethoxylation ranging from about of 4 or less. These alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4. For each of the compositions disclosed herein, having an average degree of ethoxylation of 4 or less enables the lotion of the present invention to exhibit a significant hydrophobicity, and typically exhibits an HLB of less than about 7. The hydrophobicity of the lotion is a property in delivering the benefit of cleaner skin and hair, i.e., less menses on the skin and hair or hair of the wearer.

Suitable fatty alcohol type emollients include C14-C22 fatty alcohols, preferably C16-C18 fatty alcohols. Representative examples include cetyl alcohol and stearyl alcohol, and mixtures thereof. These fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use in the present invention include polysiloxane compounds. In general suitable polysiloxane materials for use in the present invention include those having monomeric siloxane units of the following structure wherein, R1 and R2, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstantiated. R1 and R2 radicals of any particular monomeric unit may differ from the corresponding functionalities of the next adjoining monomeric unit. Additionally, the polysiloxane can be either a straight chain, a branched chain or have a cyclic structure. The radicals R1 and R2 can additionally independently be other silaceous functionalities such as, but not limited to siloxanes, polysiloxanes, silanes, and polysilanes. The radicals R1 and R2 may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes may vary as widely as the viscosity of polysiloxanes in general vary, so long as the polysiloxane is flowable or can be made to be flowable for application to the sanitary napkin topsheet. This includes, but is not limited to, viscosity as low as 5 centistokes (at 37 degrees C. as measured by a glass viscometer) to about 20,000,000 centistokes. Preferably the polysiloxanes have a viscosity at 37 degrees C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the sanitary napkin topsheets by such methods as.

Preferred polysiloxanes compounds for use in the present invention are disclosed in U.S. Pat. No. 5,059,282 (Ampulski et al), issued Oct. 22, 1991. Particularly preferred polysiloxane compounds for use as emollients in the lotion compositions of the present invention include phenyl-functional polymethylsiloxane compounds (e.g., Dow Corning 556 Cosmetic-Grade Fluid: polyphenylme-thylsiloxane) and cetyl or stearyl fictionalized dimethicones such as Dow 2502 and Dow 2503 polysiloxane fluids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Besides petroleum-based emollients, fatty acid ester emollients, fatty acid ester ethoxylates, alkyl ethoxylate emollients fatty alcohol emollients, and polysiloxanes, the emollients useful in the present invention can include minor amounts (e.g., up to about 10% of the total emollient) of other, conventional emollients. These other, conventional emollients include spermaceti or other waxes, fatty acids, and fatty alcohol ethers having from 14 to 28 carbon atoms in their fatty chain, such as stearic acid, propoxylated fatty alcohols; other fatty esters of polyhydroxy alcohols; lanolin and its derivatives. These other emollients should be included in a manner such that the solid or semisolid characteristics of the lotion composition are maintained.

The amount of emollient that can be included in the lotion composition will depend on a variety of factors, including the particular emollient involved, the lotion-like benefits desired, the other components in the lotion composition and like factors. The lotion composition can comprise from about 10 to about 95% of the emollient. Preferably, the lotion composition comprises from about 20 to about 80%, most preferably from about 40 to about 75%, of the emollient.

An especially key component of the lotion compositions of the present invention is an agent capable of immobilizing the emollient on the sanitary napkin topsheet to which the lotion composition is applied. Because the emollient in the composition has a plastic or fluid consistency at 20 degrees C., it tends to flow or migrate, even when subjected to modest shear. When applied to a sanitary napkin topsheet, especially in a melted or molten state, the emollient will not remain primarily on the surface of the topsheet. Instead, the emollient will tend to migrate and flow into the interior of the sanitary napkin.

This migration of the emollient into the interior of the sanitary napkin can cause undesired effects on the absorbency of the sanitary napkin core due to the hydrophobic characteristics of many of the emollients used in the lotion compositions of the present invention. It also means that much more emollient has to be applied to the sanitary napkin topsheet to get the desired therapeutic or protective lotion benefits. Increasing the level of emollient not only increases the cost, but also exacerbates the undesirable effect on the absorbency of the sanitary napkin core.

The immobilizing agent counteracts this tendency of the emollient to migrate or flow by keeping the emollient primarily localized on the surface of the sanitary napkin top sheet to which the lotion composition is applied. This is believed to be due, in part, to the fact that the immobilizing agent raises the melting point of the lotion composition above that of the emollient. Since the immobilizing agent is also miscible with the emollient (or solubilized in the emollient with the aid of an appropriate emulsifier), it entraps the emollient on the surface of the sanitary napkin topsheet as well.

It is also advantageous to "lock" the immobilizing agent on the surface of the sanitary napkin topsheet. This can be accomplished by using immobilizing agents which quickly crystallize (i.e., solidify) at the surface of the topsheet. In addition, outside cooling of the treated sanitary napkin topsheet via blowers, fans, etc. can speed up crystallization of the immobilizing agent.

In addition to being miscible with (or solubilized in) the emollient, the immobilizing agent needs to have a melting point of at least about 35 degrees C. This is so the immobilizing agent itself will not have a tendency to migrate or flow. Preferred immobilizing agents will have melting points of at least about 40 degrees C. Typically, the immobilizing agent will have a melting point in the range of from about 50 degrees to about 150 degrees C.

Suitable immobilizing agents for the present invention can comprise a member selected from the group consisting of C14-C22 fatty alcohols, C14-C22 fatty acids, and C14-C22 fatty alcohol ethoxylates having an average degree of ethoxylation of 4 or less, and mixtures thereof. Preferred immobilizing agents include C16-C18 fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include C16-C18 fatty acids, most preferably selected from the group consisting of palmitic acid, stearic acid, and mixtures thereof. Mixtures of palmitic acid and stearic acid are particularly preferred. Still other preferred immobilizing agents include C16-C18 fatty alcohol ethoxylates having an average degree of ethoxylation for 4 or less. Preferably, the fatty alcohols, fatty acids and fatty alcohols are linear. Again, as noted above, having an average degree of ethoxylation of 4 or less enables the lotion of the present invention to exhibit significant hydrophobicity, and typically exhibits an HLB of less than about 7. The hydrophobicity of the lotion is a property in delivering the benefit of cleaner skin and hair, i.e., less menses on the skin and hair or hair of the wearer.

Other types of immobilizing agents can be used either alone or in combination with the fatty alcohols, fatty acids, and fatty alcohol ethoxylates described above. Examples of these other types of immobilizing agents includes polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin and hair sensitivity of those using sanitary napkin topsheets to which the lotion composition is applied, these esters and amides should also be relatively mild and non-irritating to the skin and hair.

Suitable polyhydroxy fatty acid esters for use in the present invention will have the formula where in R is a C5-C31 hydrocarbyl group, preferably straight chain C7-C19 alkyl or alkenyl, more preferably straight chain C9-C17 alkyl or alkenyl, most preferably straight chain C11-C17 alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of C16-C22 saturated fatty acids. Because of the manner in which they are typically manufactured, these sorbitan esters usually comprise mixtures of mono-, di-, tri-o etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbi tan esters, e.g., sorbitan mono-, di- and tri-palmitate, sorbitan mono-, di- and tri-stearate, sorbitan mono-, di- and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and trimesters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of C16-C22 saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid ester for use in the present invention comprise certain sucrose fatty acid esters, preferably the C14-C22 saturated fatty acid esters of sucrose. Sucrose monoesters and diesters are particularly preferred and include sucrose mono- and di-strearate and sucrose mono- and di-laurate.

Suitable polyhydroxy fatty acid amides for use in the present invention will have the formula wherein R1 is H, C1-C4 hydrocarbyl, 2-hydroxyethyl, 2-hydroxypropyl, methoxyethyl, methoxypropyl or a mixture thereof, preferably C1-C4 alkyl, methoxyethyl or methoxypropyl, more preferably Cl or C2 alkyl or methoxypropyl, most preferably Cl alkyl (i.e., methyl) or methoxypropyl; and R2 is a C5-C31 hydrocarbyl group, preferably straight chain C7-C19 alkyl or alkenyl, more preferably straight chain C9-C17 alkyl or alkenyl, most preferably straight chain C11-C17 alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —CH2-(CHOH)n-CH2 OH, —CH (CH2OH)—[(CHOH)n-1]—CH2 OH, —CH2 OH—CH2-(CHOH)2 (CHOR3)(CHOH)—CH2 OH, where n is an integer from 3 to 5, and R3 is H or a cyclic or aliphatic monosaccharide. Most preferred are the glycityls where n is 4, particularly —CH2-(CHOH)4-CH2 OH.

In the above formula, R1 can be, for example, N-methyl, N-ethyl, N-propyl, N-isopropyl, N-butyl, N-2-hydroxyethyl, N-methoxypropyl or N-2-hydroxypropyl, R2 can be selected to provide, for example, cocamides, stearamides, oleamides, lauramides, myristamides, capricamides, palmitamides, tallowamides, etc. The Z moiety can be 1-deoxyglucityl, 2-eoxyfructityl, 1-deoxymaltityl, 1-deoxy-lactityl, 1-deoxygalactityl, 1-deoxymannityl, 1-deoxymal-totriotityl.

Other types of ingredients that can be used as immobilizing agents, either alone, or in combination with the above-mentioned immobilizing agents, include waxes such as carnauba, beeswax, candelilla, paraffin, ceresin, esparto, ouricuri, rezowax, and other known waxes. Preferably the wax is a paraffin wax. An example of a particularly preferred paraffin wax is Parrafin S.P. 434 from Strahl and Pitsch Inc. P.O. Box 1098 West Babylon, N.Y. 11704.

The amount of immobilizing agent that should be included in the lotion composition will depend on a variety of factors, including the particular emollient involved, the particular immobilizing agent involved, whether an emulsifier is required to solubilize the immobilizing agent in the emollient, the other components in the lotion composition and like factors. The lotion composition can comprise from about 5 to about 90% of the immobilizing agent. Preferably, the lotion composition comprises from about 5 to about 50%, most preferably from about 10 to about 40%, of the immobilizing agent.

Lotion compositions can comprise other optional components typically present in emollient, creams, and lotions of this type. These optional components include water, viscosity modifiers, perfumes, disinfectant antibacterial actives, pharmaceutical actives, film formers, deodorants, opacifiers, astringents, solvents and the like. In addition, stabilizers can be added to enhance the shelf life of the lotion composition such as cellulose derivatives, proteins and lecithin. All of these materials are well known in the art as additives for such formulations and can be employed in appropriate amounts in the lotion compositions of the present invention.

In preparing lotioned sanitary napkin products according to the present invention, the lotion composition is applied to the outer surface (i.e., body facing surface) of a sanitary napkin topsheet. Any of a variety of application methods that evenly distribute lubricious materials having a molten or liquid consistency can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the outer surface of the sanitary napkin topsheet.

The manner of applying the lotion composition to the sanitary napkin topsheet can be such that the topsheet does not become saturated with the lotion composition. If the topsheet becomes saturated with the lotion composition, there is a greater potential for the lotion to block the topsheet openings, reducing the ability of the topsheet to transmit fluid to the underlying absorbent core. Also, saturation of the topsheet is not required to obtain the therapeutic and/or protective lotion benefits. Particularly suitable application methods will apply the lotion composition primarily to the outer surface of the sanitary napkin topsheet.

The minimum level of lotion to be applied to the sanitary napkin topsheets is an amount effective for reducing the adherence of MENSES to the skin and hair of the wearer. The lotion composition is preferably applied to the sanitary napkin topsheets of the present invention in an amount ranging from about 0.1 mg/in2 to about 75 mg/in2 (6.45 mg/cm$^2$ to about 483.87 mg/cm$^2$) preferably from about 0.5 mg/in2 to about 60 mg/in2 (3.23 mg/cm$^2$ to about 387.10 mg/cm$^2$) (mg of lotion per square inch of coated topsheet) more preferably 1 mg/in$^2$ to about 60 mg/in$^2$ (6.45 mg/cm$^2$ to about 387.10 mg/cm$^2$). Because the emollient is substantially immobilized on the surface of the topsheet, less lotion composition is needed to impart the desired skin and hair care benefits. Such relatively low levels of lotion composition are adequate to impart the desired therapeutic and/or protective lotion benefits to the topsheet, yet do not saturate the topsheet's absorbency and/or wettability properties.

The lotion composition may be applied to the entire surface of the topsheet or portions thereof. The lotion composition can be applied in a stripe aligned with and centered on the longitudinal centerline of the disposable absorbent article. The lotion composition can be applied in a plurality of stripes.

The lotion composition can also be applied nonuniformly to the outer surface of the sanitary napkin topsheet. By "nonuniform" is meant that the amount, pattern of distribution, etc. of the lotion composition can vary over the topsheet surface. For example, some portions of the treated surface of the topsheet can have greater or lesser amounts of lotion composition, including portions of the surface that do not have any lotion composition on it.

The lotion composition can be applied to the topsheet at any point during assembly. For example, the lotion composition can be applied to the topsheet of the finished disposable absorbent product before it has been packaged. The lotion composition can also be applied to the topsheet before it is combined with the other raw materials to form a finished disposable absorbent product.

The lotion composition is typically applied from a melt thereof to the sanitary napkin topsheet. Since the lotion composition melts at significantly above ambient temperatures, it is usually applied as a heated coating to the topsheet. Typically, the lotion composition is heated to a temperature in the range from about 35 degrees to about 100 degrees C., preferably from 40 degrees to about 90 degrees C., prior to being applied to the sanitary napkin topsheet. Once the melted lotion composition has been applied to the sanitary napkin topsheet, it is allowed to cool and solidify to form solidified coating or film on the surface of the topsheet. Preferably, the application process is designed to aid in the cooling/set up of the lotion.

Lotion compositions of the present invention can be applied by printing methods, or continuous spray or extrusion as is known in the art, or as is disclosed in U.S. Pat. No. 5,968,025 issued to Roe et al.

It is preferred that the lotion be applied in a plurality of stripes parallel to the longitudinal axis of the absorbent article. This allows for both transfer of the lotion to a broader area of the vulva and improved fluid handling of the absorbent article.

Lotion Transfer Fluid on Skin and Hair Test Method

Figure 2:
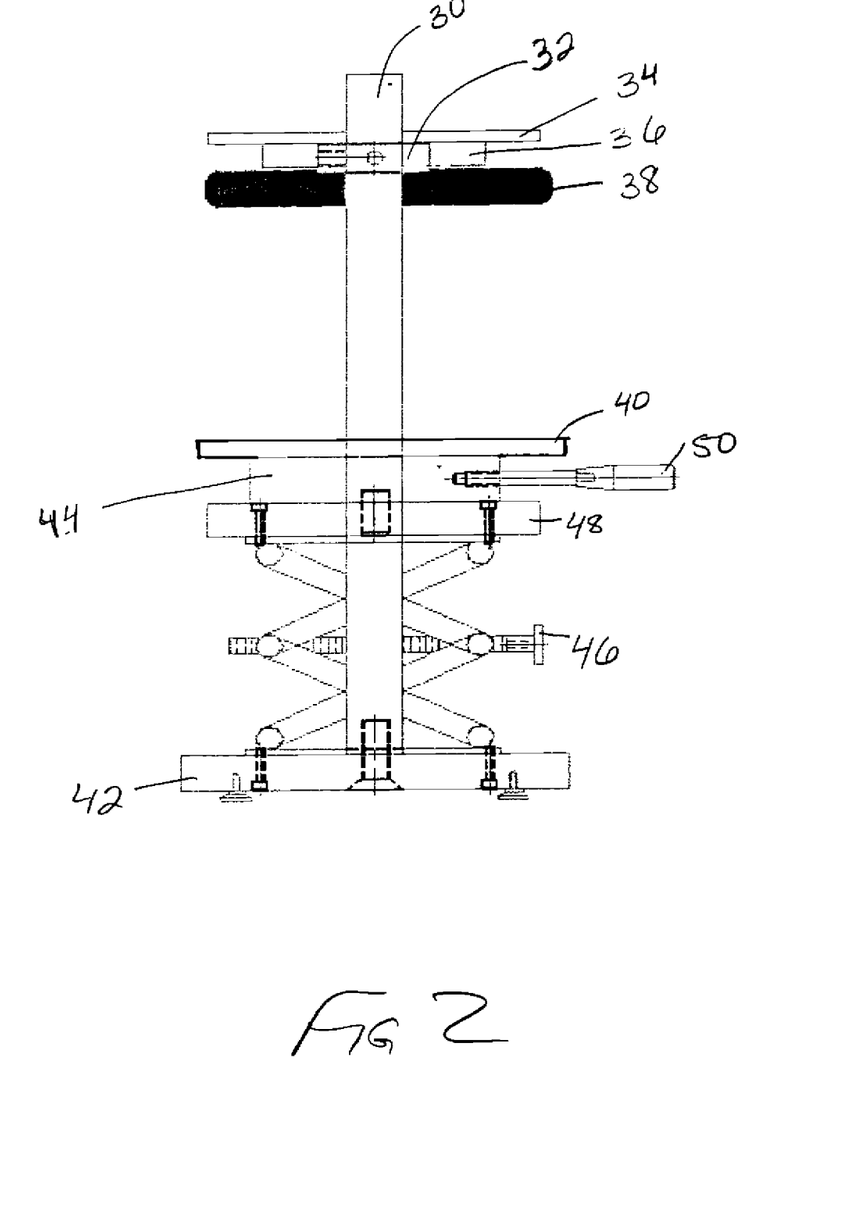
FIG. 2 is a schematic representation of a test apparatus for testing lotion transfer to skin and hair.

The following test method can be carried out using the apparatus shown in FIG. 2 to determine the lotion transfer characteristics of the present invention.

1. Apply Tegaderm™ tape strip 4"×10" (Seneca Medical, Inc. Tiffin, OH) to plexiglas plate (6"×3") so that no air bubbles exist.
2. Measure and mark the center test area (4"×2") on the Tegaderm™/Plexiglas Tegaderm™ sample holder.
3. Place sample upside down (with top of sample towards Tegaderm™) on Plexiglas/Tegaderm™ sample holder. Center lotion treated area of product on marked area.
4. Bring samples and plate to approximate body temperature by placing them in an oven at 38 C for at least 1 hour.
5. After 1 hour, place the sample (38) on the product sample holder (36) using any suitable adhesive. The product sample holder (36) is attached to a 0.25 psi weight (34)
6. Place the product sample holder (36) on top of the lab jack (42) test stand using the two guide posts (30) and stops (32) to position the sample over the motion platform (44).
7. Place the Plexiglas/Tegaderm™ sample holder (40) on motion apparatus (44) in oven. This apparatus is shown in FIG. 1 and consists of a lab jack stand (42) with a motion platform (44) on top. This motion platform (44) is circular and moves (100° total range, with a 10 cm radius) the product back and forth across the top of the Plexiglas/Tegaderm™ sample holder (40).
8. Using the knob (46) on the lab jack (42), raise the lab jack platform (48) up until it reaches the sample and lifts the product (38) and compression weight (34) off the guide post rest stops (32).
9. Once contact is made and the compression applied, begin the wiping action using the handle (50) on the motion platform (44). Make 15 wiping strokes from center and returning to center.
10. Remove Plexiglas/Tegaderm™ sample holder (40) and sample (38) from oven. Discard sample.
11. Place Plexiglas/Tegaderm™ sample holder (40) on inclined platform (15° angle) so that the fluid will run down the slope.
12. Apply 3 insults of 6 drops each (0.25 to 0.3 g total) of artificial menstrual fluid (AMF) using a disposable pipette in the center measured area.
13. Start a timer when each insult is applied.
14. Time how long it takes for each insult to move to the end of the center area or until the $3^{rd}$ drop has moved for 30 seconds.
15. Place about 6 pieces of rewet paper (2½"×4") on a top loading balance and tare balance.
16. Once the drops have all moved past the center area or 30 seconds is up on the last insult, place the rewet paper on top of the center area (leave sample at a 15° angle).
17. Apply 0.25 psi for 10 seconds to soak up the remaining AMF left in center area.
18. Weigh the amount of AMF that is picked up off the Plexiglas/Tegaderm™ sample holder and left on rewet paper using a top loading balance.

Lotion Transfer Fluid on Skin and Hair Test Results

Samples 1-3 in Table 1 were obtained from commercial Luvs diapers. Full thickness sections were cut from the lotion treated section of the diaper and used for the fluid run-off test. Samples 4-6 were feminine hygiene pads of the present invention which were coated with 56.6 gsm of lotion. Table 1 shows the grams of Artificial Menstrual Fluid remaining on the Tegaderm™ after the test.

TABLE 1

| Sample number | Grams of Artificial Menstrual Fluid |
|---|---|
| 1 | 0.09 |
| 2 | 0.08 |
| 3 | 0.12 |
| 4 | 0.04 |
| 5 | 0.04 |
| 6 | 0.04 |

As can be seen in Table 1, the Luvs diapers leave a higher amount of fluid remaining on the Tegaderm™ after the test (0.10+/−0.02 grams), than does the catamenial device of the present invention (0.04+/−0 grams), a statistically significant difference. Since this test simulates conditions of the skin and hair that are encountered when products of this type are worn menstrually, the results show that a sanitary pad of the present invention can leave less fluid on the body than absorbent products with previous lotions.

For catamenial devices the amount of lotion add on level can be significantly higher that that used in other absorbent articles, such as diapers. In one embodiment, to deliver a safe and effective amount of the lotion composition onto the skin and hair, about 19.5 mg/in2 (125.80 mg/cm$^2$) of the lotion composition can be applied to the topsheet. While not being bound by theory, it is believed that lotion can be added on at levels of 5 mg/in2, (32.26 mg/cm$^2$) 10 mg/in2 (64.52 mg/cm$^2$), 20 mg/in2 (129.03 mg/cm$^2$), 30 mg/in2 (193.55 mg/cm$^2$), 40 mg/in2 (258.06 mg/cm$^2$), 50 mg/in2 (322.58 mg/cm$^2$), 60 mg/in2 (387.10 mg/cm$^2$) or 70 mg/in2 (451.61 mg/cm$^2$). These levels refer to the area actually covered by lotion.

Example 1

A. Preparation of Lotion Compositions

A water free lotion composition is made by mixing the following melted (i.e., liquid) components together: Mineral Oil (70% wt) (Carnation White Mineral Oil, USP made by Witco Corp.), and Cetearyl Alcohol (30% wt) (a mixed linear C16-C18 primary alcohol made by the Procter & Gamble Company under the name TA-1618).

B. Preparation of Lotioned Topsheet by Hot Melt Spraying

The lotion composition is placed into a heated tank operating at a temperature of 125 degrees F. The composition is subsequently sprayed (using a Dynatec E84B1758 spray head, operating at a temperature of 165 degrees F. and an atomization pressure of 2.40 psig) onto the topsheet in two stripes of 0.5 in centered on the longitudinal axis with a spacing of 1 inch. Add-on level=0.006 g/in2 (9.3 g/m2).

Example 2

A. Preparation of Lotion Compositions

A water free lotion composition is made by mixing the following melted (i.e., liquid) components together: Petrolatum (75% wt), and Stearyl Alcohol (25% wt).

B. Preparation of Lotioned Topsheet by Hot Melt Spraying

The Lotion Composition is placed into a heated tank operating at a temperature of 51.7 degrees C. The composition is subsequently sprayed (using a Dynatec E84B1758 sprayhead, operating at a temperature of 73.9 degrees C.). and an atomization pressure of 2.40 psig) onto the topsheet in two stripes of 0.5 in centered on the longitudinal axis with a spacing of 1 inch (2.54 cm). Add-on level=0.006 g/in2 (9.3 g/m2).

Example 3

A. Preparation of Lotion Compositions

A water free lotion composition is made by mixing the following melted (i.e., liquid) components together: Petrolatum (75% wt), and Paraffin Wax (25% wt).

B. Preparation of Lotioned Topsheet by Hot Melt Spraying

The Lotion Composition is placed into a heated tank operating at a temperature of 125 degrees F. The composition is subsequently sprayed (using a Dynatec E84B1758 spray head, operating at a temperature of 165 degrees F. and an atomization pressure of 2.40 psig) onto the topsheet in five stripes of 0.2 in centered on the longitudinal axis with a spacing of 0.2 in.

What is claimed is:

1. An absorbent article comprising:
   A) a liquid impervious backsheet;
   B) a liquid pervious topsheet joined to said backsheet, said topsheet having an inner surface oriented toward the interior of said absorbent article and an outer surface oriented toward the skin and hair of the wearer when said absorbent article is being worn, wherein at least a portion of said topsheet outer surface comprises an effective amount of a lotion coating having a HLB value below 7, said lotion coating comprising:
      (i) from about 10 to about 95% of a substantially water free emollient, said emollient comprising a member selected from the group consisting of polysiloxane compounds;
      (ii) from about 5% to about 90% of an agent capable of immobilizing said emollient on said outer surface of the topsheet, said immobilizing agent being miscible with said emollient, said immobilizing agent having a melting point of at least about 35 degrees C.; and
   C) an absorbent core positioned between said topsheet and said backsheet.

2. The absorbent article of claim 1 wherein said emollient comprises a polysiloxane having the formula:

wherein, R1 and R2, for each independent siloxane monomeric unit comprises hydrogen or an alkyl, an aryl, an alkenyl, an alkaryl, an arakyl, an cycloalkyl, a halogenated hydrocarbon, or an other radical.

3. The absorbent article of claim 1 wherein said article is selected from the group consisting of feminine hygiene garments, sanitary napkins, pantiliners, and interlabial devices.

4. The absorbent article of claim 1 wherein said emollient contains about 5% or less water and comprises a petroleum based emollient selected from the group consisting of mineral oil, petrolatum, and mixtures thereof.

5. The absorbent article of claim 1 wherein said agent capable of immobilizing said emollient comprises a member selected from the group consisting of carnauba wax, beeswax, candelilla wax, paraffin wax, ceresin wax, esparto wax, ouricuri wax, rezowax, and combinations thereof.

6. The absorbent article of claim 1 wherein the quantity of lotion coating on said portion of said topsheet outer surface ranges from about 0.1 mg/in2 to about 75 mg/in2.

7. The absorbent article of claim 6 wherein the quantity of lotion coating on said portion of said topsheet outer surface ranges from about 0.5 mg/in2 to about 60 mg/in2.

8. The absorbent article of claim 1 wherein said emollient comprises a fatty acid ester emollient selected from the group consisting of methyl palmitate, methyl stearate, isopropyl laurate, isopropyl myristate, isopropyl palmitate, ethylhexyl palmitate, lauryl lactate and cetyl lactate, and mixtures thereof.

9. The absorbent article of claim 1 wherein said emollient comprises an alkyl ethoxylate emollient selected from the group consisting of C14-C18 fatty alcohol ethoxylates having an average degree of ethoxylation of 4 or less.

10. The absorbent article of claim 1 wherein said lotion coating comprises from about 5 to about 50% of said immobilizing agent, said immobilizing agent having a melting point of at least about 40 degrees C.

11. The absorbent article of claim 10 wherein said immobilizing agent comprises a C14-C22 fatty alcohol.

12. The absorbent article of claim 11 wherein said immobilizing agent comprises a C16-C18 fatty alcohol selected from the group consisting of cetyl alcohol, stearyl alcohol, and mixtures thereof.

13. The absorbent article of claim 10 wherein said immobilizing agent comprises a polyhydroxy fatty acid ester having the formula:

wherein R is a C5-C31 hydrocarbyl group; Y is a polyhydroxyhydrocarbyl moiety having a hydrocarbyl chain with at least 2 free hydroxyls directly connected to the chain; and n is at least 1.

14. The absorbent article of claim 13 wherein said immobilizing agent comprises a polyhydroxy fatty acid ester selected from the group consisting of sorbitan esters of C16-C22 saturated fatty acids, glyceryl monoesters of C16-C22 saturated fatty acids, and sucrose esters of C14-C22 saturated fatty acids.

15. The absorbent article of claim 14 wherein said immobilizing agent comprises a polyhydroxy fatty acid ester selected from the group consisting of sorbitan palmitates, sorbitan stearates, sorbitan behenates, glyceryl monostearate, glyceryl monopalmitate, glyceryl monobehenate, sucrose mono- and di-stearate, and sucrose mono- and di-laurate.

16. The absorbent article of claim 15 wherein said immobilizing agent comprises sorbitan stearates.

17. The absorbent article of claim 10 wherein said immobilizing agent comprises a polyhydroxy fatty acid amide having the formula:

wherein R1 is HX C1-C4 hydrocarbyl, 2-hydroxyethyl, 2-hydroxypropyl, methoxyethyl, methoxypropyl or a mixture thereof; R2 is a C5-C31 hydrocarbyl group; and Z is a polyhydroxyhydrocarbyl moiety having a linear hydrocarbyl chain with at least 3 hydroxyls directly connected to the chain.

18. The absorbent article of claim 17 wherein R1 is N-methyl, N-ethyl, N-propyl, N-isopropyl, N-butyl, N-2-hydroxyethyl, N-methoxypropyl or N-2-hydroxypropyl; R2 is straight chain C11-C17 alkyl or alkenyl, or mixture thereof, and Z is glycityl.

19. The absorbent article of claim 18 wherein said immobilizing agent comprises a polyhydroxy fatty acid amide selected from the group consisting of N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl, glucamide, N-tallowyl-N-methyl glucamide, and N-tallowyl-N-methoxypropyl glucamide.

20. The absorbent article of claim 10 wherein said immobilizing agent comprises a paraffin wax.

21. The absorbent article of claim 1 wherein the lotion coating is applied in a plurality of stripes parallel to a longitudinal axis of the absorbent article.

22. The absorbent article of claim 1 wherein the "Lotion Transfer Fluid on Skin and hair Test" values are less than about 0.07 g.

23. A sanitary napkin for use in a vulvar region of an adult woman, said vulvar region comprising skin and hair and being subject to contact with menstrual fluid, said sanitary napkin comprising:
A) a liquid impervious backsheet;
B) a liquid pervious, hydrophobic topsheet joined to said backsheet, said topsheet having an inner surface oriented toward the interior of said absorbent article and an outer surface oriented toward the skin and hair of the wearer when said sanitary napkin is being worn, wherein at least a portion of said topsheet outer surface comprises an effective amount of a lotion coating having a HLB value below 7 said lotion coating comprising:
(i) from about 10 to about 95% of a substantially water free emollient having a plastic or fluid consistency at 20 degrees C. wherein said emollient contains 5% or less water, said emollient comprising a member selected from the group consisting of petroleum-based emollients, fatty acid ester emollients, alkyl ethoxylate emollients, and mixtures thereof;
(ii) from about 5 to about 90% of an agent capable of immobilizing said emollient on said outer surface of the topsheet, said immobilizing agent being miscible with said emollient, said immobilizing agent having a melting point of at least about 35 degrees C. wherein said immobilizing agent is selected from the group consisting of polyhydroxy fatty acid esters, polyhydroxy fatty acid amides, C14-C22 fatty alcohols, C14-C22 fatty acids, C14-C22 fatty alcohol ethoxylates, and mixtures thereof; and
C) an absorbent core positioned between said topsheet and said backsheet.

24. The absorbent article of claim 23 wherein said article is selected from the group consisting of feminine hygiene garments, sanitary napkins, pantiliners, and interlabial devices.

25. The absorbent article of claim 23 wherein said emollient contains about 5% or less water and comprises a petroleum based emollient selected from the group consisting of mineral oil, petrolatum, and mixtures thereof.

26. The absorbent article of claim 23 wherein said agent capable of immobilizing said emollient comprises a member selected from the group consisting of carnauba wax, beeswax, candelilla wax, paraffin wax, ceresin wax, esparto wax, ouricuri wax, rezowax, and combinations thereof.

27. The absorbent article of claim 23 wherein said emollient comprises a member selected from the group consisting of polysiloxane compounds.

28. The absorbent article of claim 23 wherein the quantity of lotion coating on said portion of said topsheet outer surface ranges from about 0.1 mg/in2 to about 75 mg/in2.

29. The absorbent article of claim 27 wherein said emollient comprises a polysiloxane having the formula:

wherein, R1 and R2, for each independent siloxane monomeric unit comprises hydrogen or an alkyl, an aryl, an alkenyl, an alkaryl, an arakyl, an cycloalkyl, a halogenated hydrocarbon, or an other radical.

* * * * *